(12) United States Patent
Cao et al.

(10) Patent No.: US 7,729,754 B2
(45) Date of Patent: Jun. 1, 2010

(54) SYSTEM AND METHOD FOR ARRHYTHMIA DISCRIMINATION WITH ATRIAL-VENTRICULAR DISSOCIATION

(75) Inventors: Jian Cao, Shoreview, MN (US); Jeffrey M. Gillberg, Coon Rapids, MN (US); Troy E. Jackson, New Brighton, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 686 days.

(21) Appl. No.: 11/554,323

(22) Filed: Oct. 30, 2006

(65) Prior Publication Data

US 2008/0103404 A1  May 1, 2008

(51) Int. Cl.
*A61B 5/04* (2006.01)
(52) U.S. Cl. .................................................. 600/518
(58) Field of Classification Search .................. 607/14, 607/26, 4, 5, 9, 17; 600/518, 519, 515, 516
See application file for complete search history.

(56) References Cited

U.S. PATENT DOCUMENTS

| | | | |
|---|---|---|---|
| 4,860,749 A | 8/1989 | Lehmann | |
| 5,280,792 A | 1/1994 | Leong et al. | |
| 5,325,856 A * | 7/1994 | Nitzsche et al. | 600/516 |
| 5,327,900 A | 7/1994 | Mason et al. | |
| 5,350,406 A * | 9/1994 | Nitzsche et al. | 607/14 |
| 5,466,245 A * | 11/1995 | Spinelli et al. | 607/17 |
| 5,545,186 A | 8/1996 | Olson et al. | |
| 5,620,471 A * | 4/1997 | Duncan | 607/14 |
| 5,755,737 A * | 5/1998 | Prieve et al. | 607/4 |
| 5,855,593 A | 1/1999 | Olson et al. | |
| 5,978,700 A | 11/1999 | Nigam | |
| 6,141,581 A | 10/2000 | Olson et al. | |
| 6,178,350 B1 | 1/2001 | Olson et al. | |
| 6,259,947 B1 | 7/2001 | Olson et al. | |
| 6,487,443 B2 | 11/2002 | Olson et al. | |
| 6,748,269 B2 | 6/2004 | Thompson et al. | |
| 6,889,080 B2 * | 5/2005 | Henry et al. | 607/14 |

(Continued)

FOREIGN PATENT DOCUMENTS

JP  07148129 A  *  6/1995

OTHER PUBLICATIONS

Curione M et al: "An electrocardiographic criterion to detect AV dissociation in wide QRS tachyarrhythmias." XP002498551, Database Medline(Online) US National Library of Medicine, Apr. 1988-04.

(Continued)

*Primary Examiner*—George R Evanisko
*Assistant Examiner*—Hiba El-Kaissi
(74) *Attorney, Agent, or Firm*—Stephen W. Bauer

(57) ABSTRACT

Ventricular arrhythmias are monitored and classified based upon various criteria. One criterion is PR dissociation which is determined by comparing the PR interval in a current RR cycle to a median PR value. If the current PR interval varies too far from the median, then dissociation is indicated. Often, there are multiple atrial events in a given RR interval and the PR value has been based upon the last atrial event in the cycle. An algorithm determines whether to use the last atrial event in a cycle or whether an earlier atrial event occurred and would provide a more accurate PR value.

20 Claims, 6 Drawing Sheets

U.S. PATENT DOCUMENTS

| | | | |
|---|---|---|---|
| 7,103,405 B2 * | 9/2006 | Sarkar et al. | 600/518 |
| 2002/0169483 A1 * | 11/2002 | Henry et al. | 607/5 |
| 2003/0144700 A1 * | 7/2003 | Brown et al. | 607/14 |
| 2004/0111120 A1 * | 6/2004 | Sarkar et al. | 607/5 |
| 2005/0010257 A1 | 1/2005 | Lincoln et al. | |
| 2007/0093874 A1 * | 4/2007 | Chirife et al. | 607/25 |
| 2008/0062880 A1 * | 3/2008 | Yew et al. | 370/235 |

OTHER PUBLICATIONS

International Search Report, PCT/US2007/081575, Oct. 31, 2008, 7 Pages.

* cited by examiner

SYSTEM AND METHOD FOR ARRHYTHMIA DISCRIMINATION WITH ATRIAL-VENTRICULAR DISSOCIATION

BACKGROUND

The present invention relates generally to implantable medical devices (IMDs) and more specifically to implantable cardioverter defibrillators (ICDs) that sense cardiac parameters and are capable of delivering a high energy therapy to cardiovert or defibrillate a heart.

DESCRIPTION OF THE RELATED ART

ICDs are well known, cost effective, life saving medical devices that provide various cardiac therapies including pacing, cardioversion and/or defibrillation. Pacing is most commonly provided for bradycardia; however, there are numerous pacing therapies useful with tachycardia such as overdrive pacing and anti-tachy pacing (ATP). Defibrillation delivers a high energy waveform across a portion of the heart, often on the order of 20-40 joules. Defibrillation interrupts a chaotic rhythm, such as for example, atrial or ventricular fibrillation, and allows a normal sinus rhythm to emerge intrinsically or via subsequent pacing.

As indicated, tachycardia may originate from the atria, the ventricles or both simultaneously (double tachycardia). An arrhythmia in either the ventricles or the atria may affect the other. That is, an abnormally fast atrial rhythm may conduct to the ventricles causing a correspondingly high ventricular rate. Conversely, an abnormally fast ventricular arrhythmia may conduct retrograde into the atria. Thus, while it is generally easy to identify that some type of arrhythmia is occurring, there is sometimes a challenge in identifying its true nature and origin.

As a generalization, ventricular tachycardia is more serious and often requires more immediate therapy than atrial tachycardia. That is, sinus tachycardia, atrial fibrillation (AF), and atrial flutter (AFL) may be tolerated whereas ventricular tachycardia (VT), fast ventricular tachycardia (FVT), and ventricular fibrillation (VF) may immediately lead to significant hemodynamic compromise or sudden cardiac arrest (SCA) depending upon the specific condition, rate, etc.

The general distinction between the immediate affect of atrial versus ventricular tachycardia as well as the gradation of seriousness in ventricular tachycardia provide for several therapy options. First, in some instances therapy may be withheld and the condition may self correct or may be tolerated by the patient. For example, AF may spontaneously terminate. Second, less aggressive therapies may be provided such as overdrive pacing, ATP, or drug titration. Some of these less aggressive options may be appropriate in atrial tachycardia and with some VT, provided the rate is below a threshold. Finally, the most aggressive therapy is the delivery of a high energy defibrillation shock, which is highly effective. It should also be appreciated that prior to delivering defibrillation, ATP may be provided while the ICD prepares. The ATP may terminate the arrhythmia in some cases before the device actually delivers defibrillation, which then inhibits that delivery.

The basic guiding principle for defibrillation is to deliver the therapy whenever necessary, withhold when not necessary, and deliver if uncertain. As indicated, some events such as AF may self terminate or other therapies terminate the AF and many IMDs provide patients with the ability to elect or withhold defibrillation for AF and similar arrhythmias. This is important in that defibrillation therapy can be uncomfortable.

Further, from a physical and psychological perspective there may be patient frustration in receiving defibrillation therapy for misclassified events. From a device perspective, the delivery of unnecessary therapy depletes the internal power supply.

Thus, modern ICDs need to provide therapy delivery capabilities but must also provide accurate and reliable sensing and arrhythmia discrimination capabilities. The various device manufacturers have algorithms to interpret the sensed cardiac data and take appropriate actions. These algorithms are improved, varied and modified as new therapies, diagnostic capabilities, or sensory inputs are provided. There is also a basic underlying set of rules that form the core of the discrimination algorithm. One example is referred to as PR Logic™, as used by Medtronic, Inc. in many of their ICDs. Certain embodiments of this algorithm are described in U.S. Pat. Nos. 6,487,443; 6,259,947; 6,141,581; 5,855,593; and 5,545,186 each to Olson et al. and assigned to Medtronic, Inc and all are herein incorporated by reference in their entireties.

DETAILED DESCRIPTION

Figure 1:
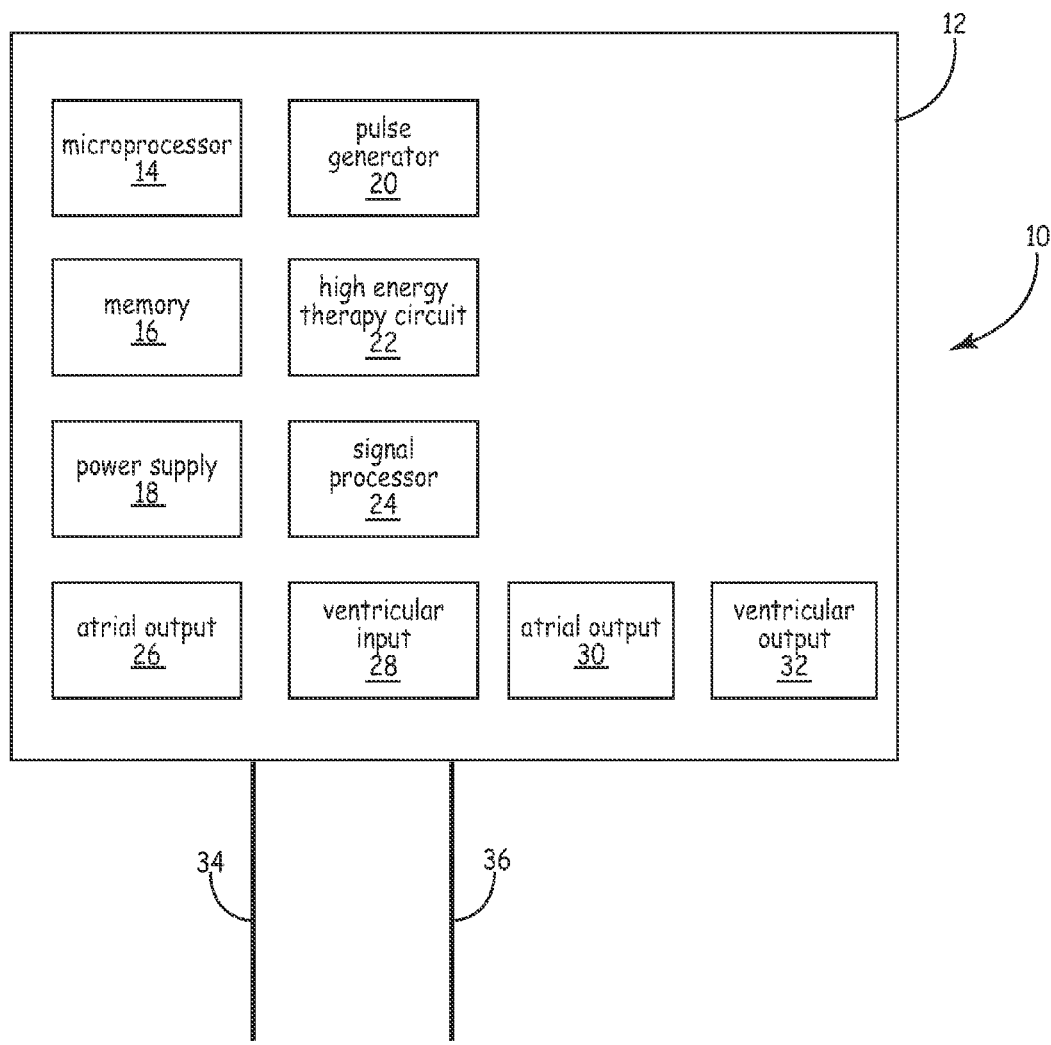
FIG. 1 is a block diagram of an implantable cardiac defibrillator (ICD).

FIG. 1 is a block diagram of an ICD 10 and the various operably interconnected components and modules. ICD 10 includes a housing 12 containing a microprocessor 14, memory 16, and a power supply 18, such as a battery. Also included is a pulse generator 20, a high energy therapy circuit 22 for providing defibrillation, a signal processor 24 to process data received via an atrial input 26 and a ventricular input 28 according to algorithms retained in memory 16, encoded into firmware or otherwise provided. An atrial output module 30 and ventricular output module 32 are provided to control delivered therapies, typically via atrial lead(s) 34 and ventricular lead(s) 36. FIG. 1 is not meant to illustrate each component of an ICD as this is generally well known in the art. It should be appreciated that the present invention may be utilized in a classic ICD having a housing implanted subcutaneously or submuscularly with lead(s) extending into the heart transvenously or extending to an epicardial portion or the heart. Alternatively, the present invention may be utilized in an implantable subcutaneous defibrillator that is without having lead transvenously implanted into or onto the heart. In one embodiment, the microprocessor 14 includes instructions that when executed by the microprocessor 14 cause the ICD 10 to perform the invention.

Figure 2:
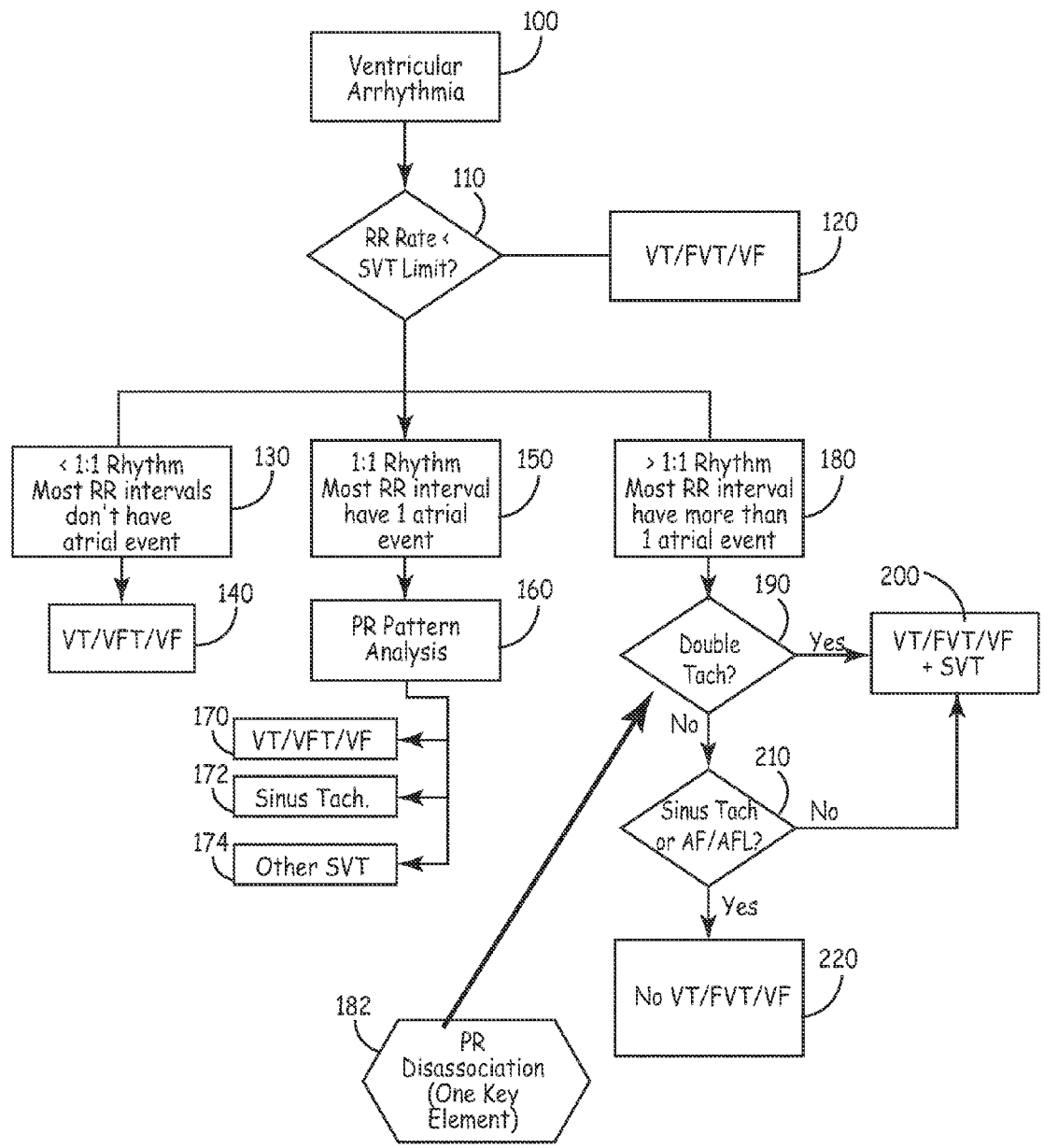
FIG. 2 is a flowchart of a process for broadly classifying tachycardia.

FIG. 2 is a highly simplified overview of a decision tree useful in classifying arrhythmias, according to a set of rules such as PR Logic™. This process is set out in greater detail in Singer's *Interventional Electrophysiology*, $2^{nd}$ edition (June, 2001), Chapter 21 titled "Dual-Chamber Sensing and Detection for Implantable Cardioverter-Defibrillators", by Gillberg and Olson, which chapter is herein incorporated by reference in its entirety. Each ventricular interval (i.e., an R-R interval) is a discrete unit that is evaluated and at block 100, a determination is made that there is some evidence of a possible ventricular arrhythmia. The ICD 10 evaluates the R-R intervals based upon an historic or expected value, such as a median value of a predetermined number of immediately prior cycles (e.g., 12 R-R intervals). This median R-R value is one parameter that may be used to initially trigger the ventricular arrhythmia indication (100). The ICD 10 compares (110) the median R-R interval to an SVT (supraventricular tachycardia) limit. If the median R-R interval value is under (i.e., rate is faster; thus, the interval is shorter) the SVT limit, then the ICD 10 determines that VT, FVT or VF is occurring and provides defibrillation. In other words, the ventricular rate is so high that immediate therapy is warranted and further discrimination of the arrhythmia is not provided.

Alternatively, the median R-R interval may be above the SVT limit (110) and further discrimination is permitted. The easiest type of rhythm to classify is designated as "less than" a one to one rhythm (130). That is, most of the R-R intervals are devoid of any atrial activity. This is a strong indication that the arrhythmia is VT, FVT, or VF (140) and again, therapy is delivered.

The next class of rhythms is designated as 1:1 (150). That is, most R-R intervals include a single atrial event. The ICD 10 performs a pattern analysis algorithm (160) based on the PR interval and is able to discriminate between VT/VFT/VF (170), sinus tachycardia (172), or other SVTs (174). This is a highly simplified overview as a more detailed description of the PR pattern analysis (160) is not required for the present invention and various examples are provided in the material incorporated by reference. In addition, other mechanisms for discriminating 1:1 rhythms are available and may be employed herein.

The third class of rhythms is designated as having a greater than 1:1 correlation. That is, most of the R-R intervals have more than 1 atrial event. This may mean, for example, that out of every 5 R-R intervals, at least three (3) of those intervals have two (2) or more atrial events. This is the most complex type of rhythm to further discriminate. The first step (180) is to determine if double tachycardia is occurring; if so, VT/FVT/NF is occurring and therapy is delivered (200). That is, if double tachycardia is present then by definition both the atria and the ventricles have tachy rhythms and the appropriate therapy for the relevant ventricular rhythm is provided (e.g., defibrillation). An important element in determining if double tachycardia is occurring is PR dissociation (182). Association or dissociation means that a given atrial event (P) is associated with a subsequent ventricular event (R). That is, that atrial event (P) conducted and initiated the ventricular event (R). If there is PR dissociation, then the ventricular depolarization is occurring independently from the atrial event. As a generalization, if there is PR dissociation this indicates VT/FVT/VF and if there is PR association then the event is likely SVT. Again, this description is grossly simplified and discrimination criteria other than PR dissociation (182) are used to fully determine double tachycardia (180). These criteria include PR patterning, RR regularity, and a determination of the ventricular arrhythmia component (e.g., is it VF or VT).

If there is no double tachycardia (180), the next step is to determine (210) if there is ST (sinus tachycardia) or AF/AFL (atrial fibrillation/atrial flutter). The ICD 10 utilizes various discrimination criteria such as PR patterning, PP irregularity, FFRW oversensing (far field R wave), and RR regularity in making this determination. If present, then the ICD 10 may determine (220) that there is no VT/FVT/VF and withhold therapy. Conversely, if not present then this indicates that VT/FVT/VF is present (200).

Evidence of PR dissociation (182) is an important criterion in identifying double tachycardia (180), among other things. It is important to remember that each discrete R-R interval is evaluated but conclusions are typically made based upon data collected over a plurality of intervals. As indicated, a running median R-R interval is maintained. In order to be in the "greater than 1:1" decision tree a certain number of intervals must have had more than one atrial event. Thus, each R-R interval may be classified and these discreet classifications are then used in combination.

Figure 3:
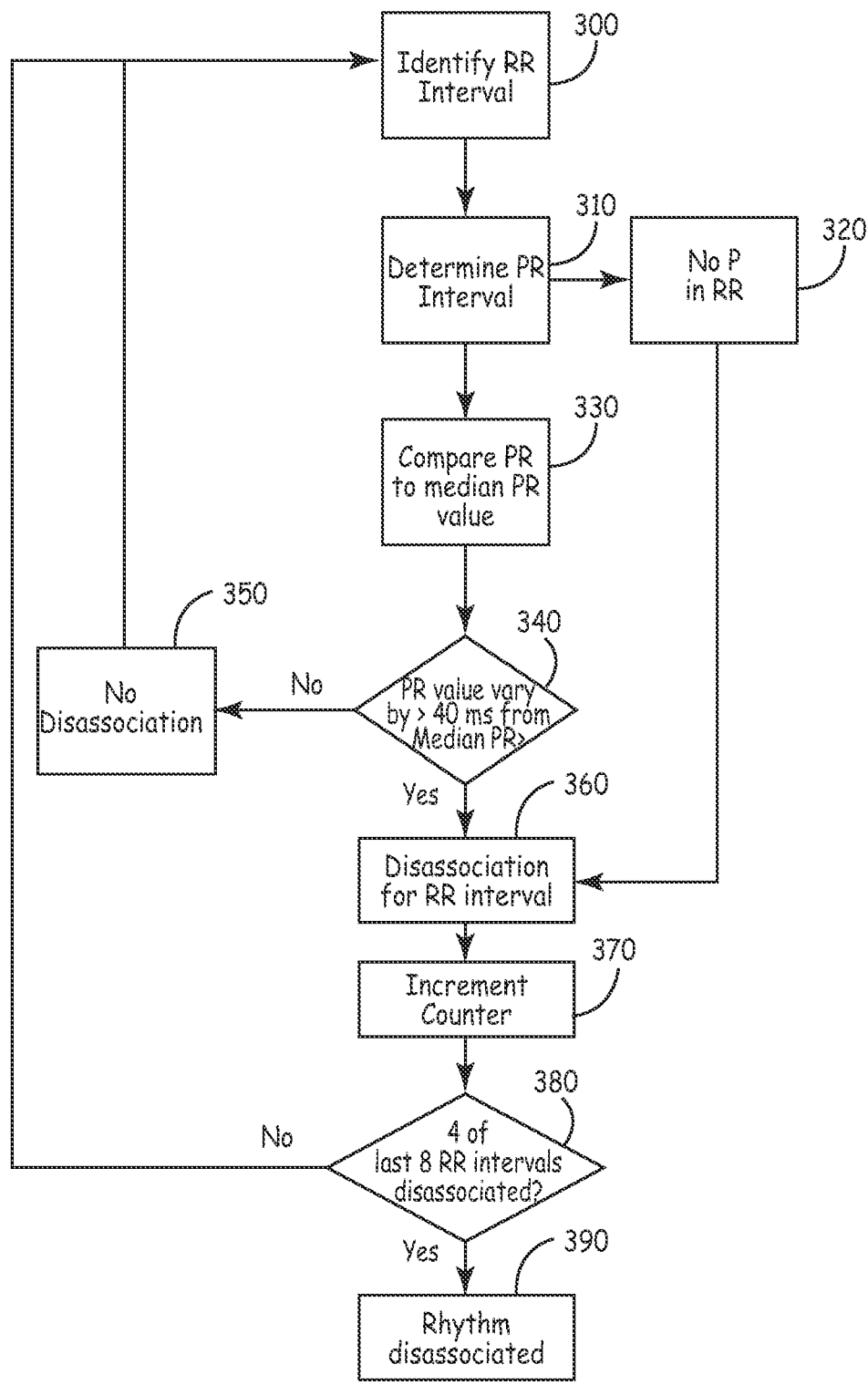
FIG. 3 is a flowchart describing one process for determining PR dissociation.

FIG. 3 is a flowchart describing a process of determining if a given R-R interval is dissociated and if an overall rhythm is dissociated. The process begins (300) with an identification of an R-R interval. Then the PR interval is determined (310). This is the time interval from the last atrial event within the R-R interval to the second R event. While most events will have multiple atrial events, there may be R-R intervals that have no atrial (P) events (320). If this is the case, then this particular cycle is classified as dissociated (360).

Assuming there was a PR interval, this interval is compared with an historic or target PR value, such as a median PR value (330). The median PR interval is based upon a predetermined number of cycles, such as the last 12 R-R intervals. The comparison (340) includes determining a difference between the current PR interval and the median PR interval. If the absolute value of this difference exceeds some predetermined quantity (e.g., 40 ms) then the current R-R cycle is classified as dissociated (360). Conversely, if the current PR interval is within 40 ms of the median, then the R-R interval is not classified as dissociated (350) and the process continues. The median value is updated accordingly.

Returning to step (360), if the R-R interval is classified as dissociated then a counter is incremented (370) and the ICD 10 determines (380) if the criteria is met to classify the rhythm as dissociated. In this example, the criteria are whether 4 of the last 8 R-R intervals were each individually dissociated. If not, the process returns to step (300), if so then the ICD 10 classifies (390) the rhythm as being dissociated. This parameter (positive or negative) is used, for example, in the arrhythmia discrimination as described in FIG. 2 where PR dissociation is relevant.

This determination of PR dissociation is generally useful; however, there are certain situations where incorrect results are returned which could lead to inappropriate therapies being delivered. It should be noted that when an error is made, it is on the side of caution with the delivery of therapy as opposed to withholding therapy. That said, it would be preferable to avoid unnecessary shocks.

Figure 4:
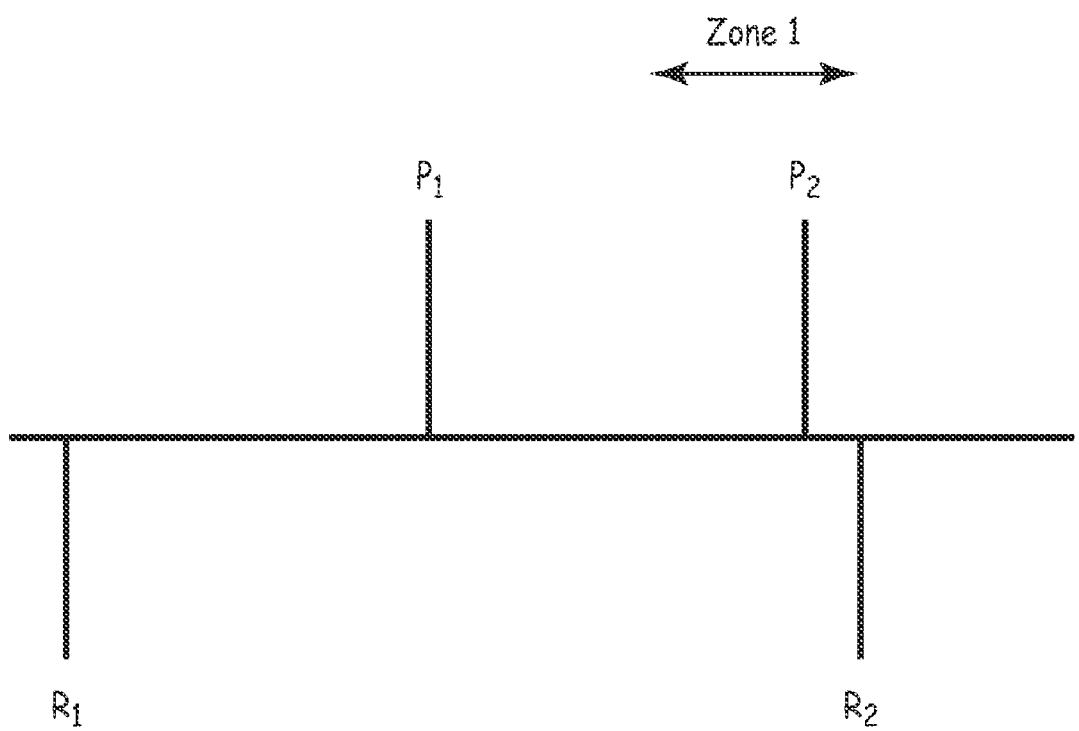
FIG. 4 is a timing diagram illustrating an R-R interval with multiple atrial events.

FIG. 4 illustrates a given R-R interval (R1-R2). There are two atrial events P1 (penultimate), P2 (final). In the process described in FIG. 3, the PR interval would be P2-R2 and would likely be dissociated from a median PR interval. P2 is the final atrial event that precedes in time the ventricular event R2; however, P2 is not clinically meaningful with respect to R2 because it is too close in time to have conducted. That is, the present invention provides for a consideration zone or consideration value, which in one embodiment is 60 ms. It should be appreciated that the numerical value may be varied while remaining within the scope of the present invention. Atrial events within the consideration zone are given further scrutiny in the dissociation determination.

Figure 5:
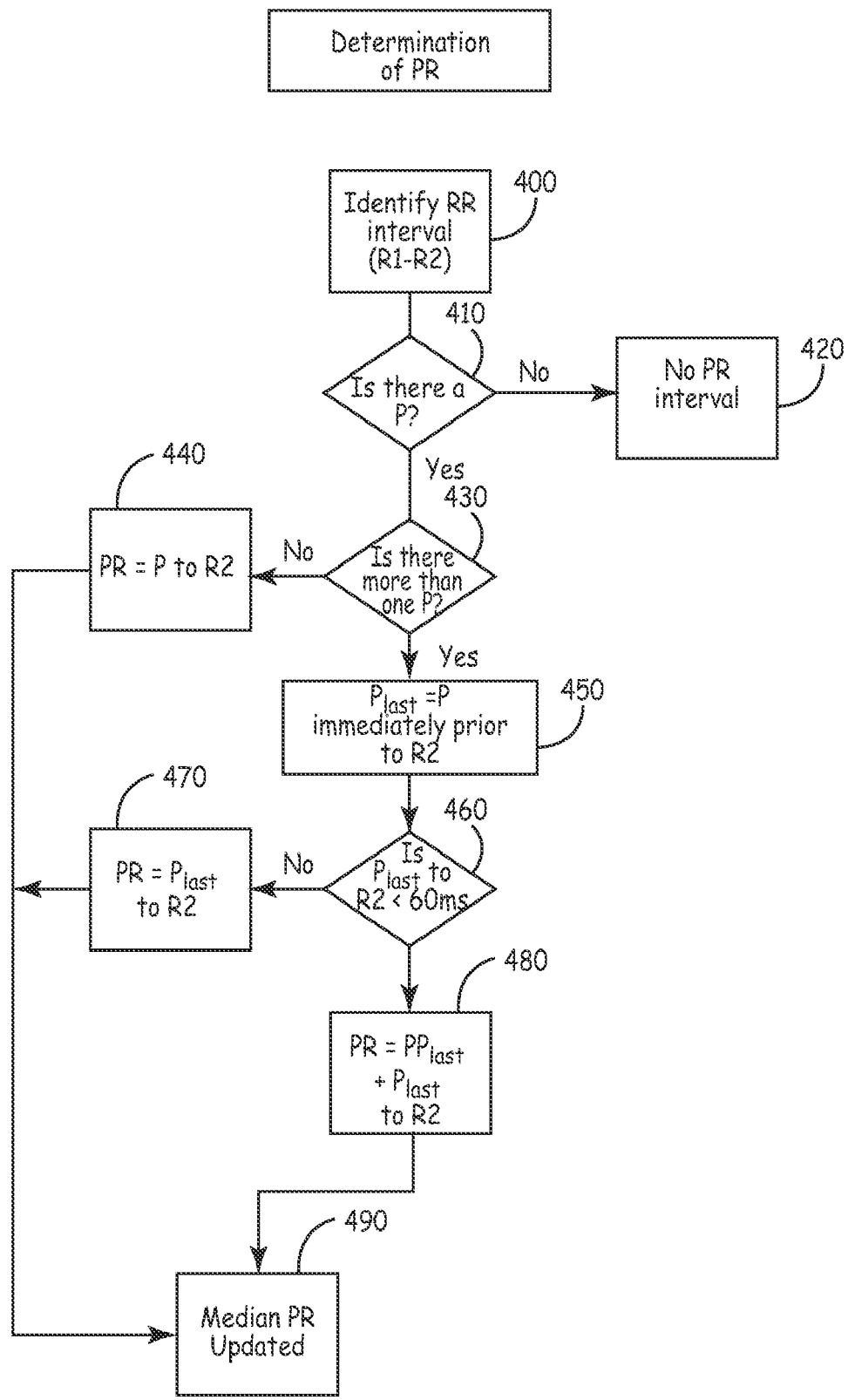
FIG. 5 is a flowchart describing a process for determining a PR interval within an R-R interval.

FIG. 5 is a flowchart describing a method of determining a PR interval that is then utilized in the dissociation process of FIG. 3. Once again, the individual R-R interval (R1-R2) is identified (400). The ICD 10 determines (410) if there was an atrial event (P) in the R1-R2 interval. If not (420), there is no PR interval and the RR interval is dissociated (FIG. 3). If there was an atrial event (410), the ICD 10 determines if there was more than one atrial event P within the same R1-R2 interval. If not, then the PR interval is equal to P to R2 (regardless of whether P is within the consideration zone).

If there is more then one atrial event, the one immediately prior to R2 is designated (450) as $P_{last}$. Then, the interval from $P_{last}$ to R2 is calculated and if greater than, e.g., 60 ms this value is used as the PR interval for R1-R2. That is, if $P_{last}$ is outside the consideration zone (e.g., 60 ms), the ICD 10 uses this value to determine the PR interval. If the interval from $P_{last}$ to R2 is less than or equal to 60 ms, then the penultimate atrial event prior to R2 and therefore logically immediately prior to $P_{last}$ is identified ($P_{second}$) and the interval between the two is designated as: $P_{second}-P_{last}$. The PR interval for R1-R2 is set (480) as:

$$PR_{(R1\ to\ R2)} = ((P_{second}\ to\ P_{last}) + (P_{last}\ to\ R2));$$

or equivalently $$PR_{(R1\ to\ R2)} = P_{second}\ to\ R2.$$

From either step (470) or (480), the median PR interval is updated and the determined PR interval for R1-R2 is used in the process of FIG. 3. It should be appreciated that in an alternative embodiment, the ICD 10 may determine the PR value immediately upon first evaluating the R-R interval if the immediately prior atrial event (as compared with R2) is outside of the consideration zone, without further analysis of other atrial events that may have occurred in the same R-R interval.

Figure 6:
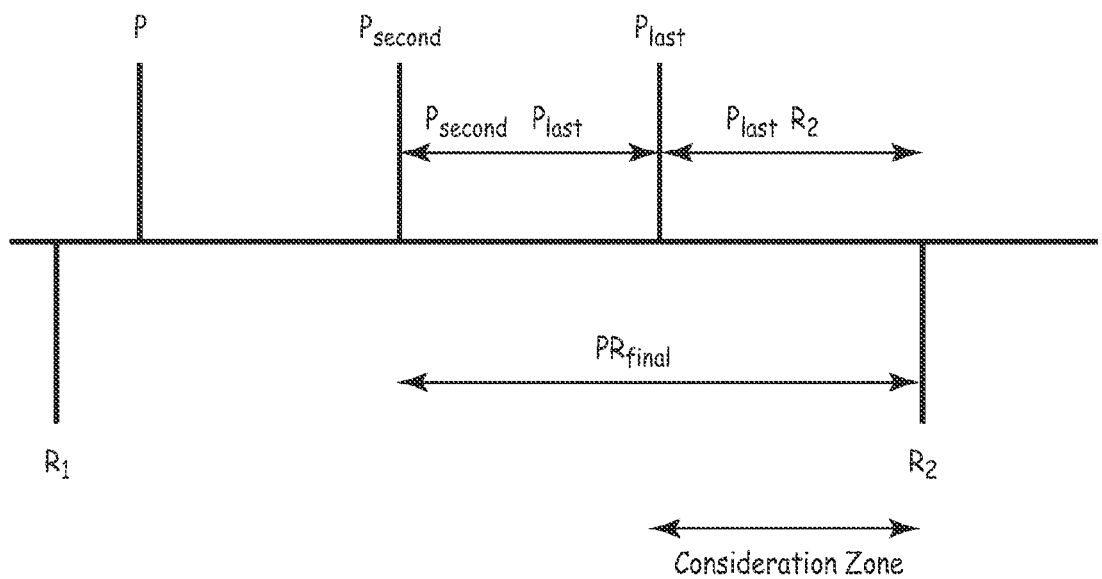
FIG. 6 is a timing diagram that graphically illustrates certain concepts of the process from FIG. 5.

FIG. 6 is a timing diagram that graphically illustrates an example of the above with R1-R2 having multiple atrial events and $P_{last}$ being within the consideration zone (e.g., 60 ms) thus, leading to the consideration of $P_{second}$. $PR_{final}$ therefore becomes $P_{second}$—R2 which is also the same as (($P_{second}$ to $P_{last}$)+($P_{last}$ to R2)). It should be appreciated that even more atrial events may occur in R1-R2, as illustrated, however only the two prior to R2 are generally utilized. In one optional embodiment, if more that two atrial events are sensed and/or present within the consideration zone, then $P_{second}$ will be the latest occurring atrial event outside the consideration zone.

When $P_{last}$ is within the consideration zone, it means that it was unlikely to have conducted and result in the ventricular depolarization R2. If it was the sole atrial event, the conclusion drawn of dissociation is therefore accurate. However, when there is a second (earlier) atrial event $P_{second}$ it is quite possible that this event conducted and resulted in R2. Thus, this is a more accurate PR interval to consider in this R-R interval. Ultimately, if neither resulting PR interval is within, e.g., 40 ms of the median PR value, dissociation will be indicated; however, the number of falsely indicated dissociated events will be reduced as compared with a determination based solely upon the last atrial event in a given R-R interval. As dissociation is an indicator of VT/FVT/NF, improperly classifying an interval as dissociated may contribute to unnecessary shocks and conversely, improving the accuracy of dissociation determinations will reduce the number of unnecessary shock thereby improving patient satisfaction with the implantable medical device.

While various embodiments have been shown and described it should be appreciated that one of ordinary skill in the art would recognize various variations of these embodiments as being within the scope and spirit of the present invention. Further, various combinations of elements and embodiments may be made, though not specifically illustrated while also remaining within the spirit and scope of the present invention.

The invention claimed is:

1. A method of determining PR dissociation comprising:
   sensing atrial events (P-waves) and ventricular events (R-waves);
   generating a target PR value from a plurality of preceding R-R intervals;
   identifying a given R-R interval;
   setting a current PR interval for the given R-R interval to a first duration defined as the interval between a final atrial event and a final ventricular event of the given R-R interval if the first duration exceeds a consideration value and setting the current PR interval to a second duration if the first duration is equal to or less than the consideration value, wherein the second duration is equal to the first duration plus a PP interval defined as the interval between a penultimate atrial event in the given R-R interval and the final atrial event;
   comparing the current PR interval to the target PR value;
   determining if the current PR interval is dissociated based upon the comparison; and
   delivering therapy to a patient based upon the determination of dissociation.

2. The method of claim 1, further comprising updating the target PR value with the current PR value for an R-R interval subsequent to the given R-R interval.

3. The method of claim 1, wherein the target PR value is a median of PR intervals from a predetermined number of RR intervals.

4. The method of claim 1, wherein the consideration value is approximately equal to 60 ms.

5. The method of claim 1, wherein comparing includes obtaining an absolute value of a difference between the target PR value and the current PR interval and determining further includes indicating dissociation if the absolute value of the difference exceeds a first predetermined value.

6. The method of claim 5, wherein the first predetermined values is approximately 40 ms.

7. The method of claim 1, further comprising:
   determining if there were no atrial events, a single atrial event, or multiple atrial events within the given R-R interval;
   classifying the given R-R interval as dissociated if there were no atrial events within the given R-R interval; and
   setting the current PR interval equal to the duration between the single atrial event and the end of the given R-R interval.

8. The method of claim 1, further comprising:
   detecting a greater than 1:1 tachyarrhythmia; and
   utilizing the determination of dissociation in discriminating between atrial and ventricular arrhythmia.

9. The method of claim 8, wherein discriminating between atrial and ventricular arrhythmias includes identifying whether or not a double tachyarrhythmia is occurring.

10. An implantable medical device (IMD) comprising:
    means for sensing atrial events (P-waves) and ventricular events (R-waves);
    means for generating a target PR value from a plurality of preceding R-R intervals;
    means for identifying a given R-R interval;
    means for setting a current PR interval for the given R-R interval to a first duration defined as the interval between a final atrial event and a final ventricular event of the given R-R interval if the first duration exceeds a consideration value and setting the current PR interval to a second duration if the first duration is equal to or less than the consideration value, wherein the second duration is equal to the first duration plus a PP interval defined as the interval between a penultimate atrial event in the given R-R interval and the final atrial event; and means for comparing the current PR interval to the target PR value; and means for determining if the current PR interval is dissociated based upon the comparison.

11. The IMD of claim 10, wherein the consideration value is approximately equal to 60 ms.

12. The IMD of claim 10, wherein the means for comparing further include means for obtaining an absolute value of a difference between the target PR value and the current PR interval and indicating dissociation if the absolute value of the difference exceed a first predetermined value.

13. The IMD of claim 10, further comprising:

means for determining if there were no atrial events, a single atrial event, or multiple atrial events within the given R-R interval;

means for classifying the given R-R interval as dissociated if there were no atrial events within the given R-R interval; and means for setting the current PR interval equal to the duration between the single atrial event and the end of the given R-R interval.

14. A non-transitory computer readable medium comprising instructions that when executed on a processor of an implantable medical device (IMD), cause the IMD to:

sense atrial events (P-waves) and ventricular events (R-waves);

generate a target PR value from a plurality of preceding R-R intervals;

identify a given R-R interval;

set a current PR interval for the given R-R interval to a first duration defined as the interval between a final atrial event and a final ventricular event of the given R-R interval if the first duration exceeds a consideration value and setting the current PR interval to a second duration if the first duration is equal to or less than the consideration value, wherein the second duration is equal to the first duration plus a PP interval defined as the interval between a penultimate atrial event in the given R-R interval and the final atrial event;

compare the current PR interval to the target PR value; and determine if the current PR interval is dissociated based upon the comparison.

15. The computer readable medium of claim 14, wherein the instructions further cause the IMD to update the target PR value with the current PR value for an R-R interval subsequent to the given R-R interval.

16. The computer readable medium of claim 14, wherein the target PR value is a median of PR intervals from a predetermined number of RR intervals.

17. The computer readable medium of claim 14, wherein the consideration value is approximately equal to 60 ms.

18. The computer readable medium of claim 14, wherein when the instructions cause the IMD to compare, the IMD further obtains an absolute value of a difference between the target PR value and the current PR interval and indicates dissociation if the absolute value of the difference exceed a first predetermined value.

19. The computer readable medium of claim 18, wherein the first predetermined value is approximately 40 ms.

20. The computer readable medium of claim 14, wherein the instructions further cause the IMD to:

determine if there were no atrial events, a single atrial event, or multiple atrial events within the given R-R interval;

classify the given R-R interval as dissociated if there were no atrial events within the given R-R interval; and set the current PR interval equal to the duration between the single atrial event and the end of the given R-R interval.

* * * * *